United States Patent

Akpan et al.

[11] Patent Number: 5,967,660
[45] Date of Patent: Oct. 19, 1999

[54] ACCELERATED THERMAL FATIGUE TESTING OF ENGINE COMBUSTION CHAMBERS

[75] Inventors: Edward Akpan, Novi; Jeff Lee Branson, Dearborn; Blake Ross, Ann Arbor, all of Mich.; John Loncke, Lasalle, Canada; Long T. Dinh, Lasalle, Canada; Richard Piekos, Lasalle, Canada

[73] Assignee: Ford Global Technologies, Inc., Dearborn, Mich.

[21] Appl. No.: 08/996,248

[22] Filed: Dec. 22, 1997

Related U.S. Application Data

[63] Continuation of application No. 08/870,209, Jun. 6, 1997.
[51] Int. Cl.$^6$ ............................. G01N 3/60; G01M 15/00; F27D 19/00
[52] U.S. Cl. ................................. 374/57; 73/119; 432/51
[58] Field of Search ...................... 374/45–57; 73/118.1; 432/51–57

[56] References Cited

U.S. PATENT DOCUMENTS

| | | |
|---|---|---|
| 3,599,475 | 8/1971 | Dubouch . |
| 3,973,429 | 8/1976 | Durgan et al. . |
| 4,090,401 | 5/1978 | Yamamoto . |
| 4,171,636 | 10/1979 | Bergeron . |
| 4,213,328 | 7/1980 | Roeschlaub et al. . |
| 5,054,314 | 10/1991 | Cofflard et al. . |
| 5,269,370 | 12/1993 | Christian et al. . |

FOREIGN PATENT DOCUMENTS 1460639  2/1989  Russian Federation .

*Primary Examiner*—Vit Miska
*Attorney, Agent, or Firm*—Joseph W. Malleck

[57] ABSTRACT

A method and apparatus of providing accelerated thermal fatigue testing of an engine component, comprising: (i) impinging one or more torch flames directly on a selected area of the test specimen (i.e. metallic engine cylinder head) to heat such area to a critical test temperature that exceeds the normal maximum loading temperature of the specimen in normal use by about 10–25%, and holding such temperature for a period of 0.01–2.0 minutes; (ii) at the end of the holding period (ie. Water jet water in head jacket, or air in ports) quenching the heated area of the test specimen to a temperature that is about 75% below that of the normal maximum loading temperature and holding such quenching temperature for about 1–3 minutes; and (iii) repeating steps (i) and (ii) until a crack is induced in the test specimen while recording the history of temperature and time involved in such repeated steps.

8 Claims, 3 Drawing Sheets

# ACCELERATED THERMAL FATIGUE TESTING OF ENGINE COMBUSTION CHAMBERS

This application is a continuation of earlier filed U.S. application Ser. No. 08/870,209 filed Jun. 6, 1997 entitled "ACCELERATED THERMAL FATIGUE TESTING OF ENGINE COMBUSTION CHAMBER".

TECHNICAL FIELD

This invention relates to the technology of testing cylinder heads of internal combustion engines for endurance and more particularly to testing for fatigue strength under thermally fatiguing conditions.

DISCUSSION OF THE PRIOR ART

To determine fatigue life, a thermal fatigue crack must be generated in the test specimen while monitoring time and stress. Testing of internal combustion engine cylinder heads containing combustion chamber walls has required head specimens assembled as an engine to be run on dynamometers under regular engine operating conditions until cracks appear; this requires an inordinately long time period to eventually determine the fatigue life, accompanied with very high cost; usually three to four months and high personnel expenses are involved.

Suggestions have been made in the prior art to shorten the dynamometer testing procedure by attempting to increase the temperature at which the specimen head is tested to accelerate the procedure by restricting the cooling water in the head; this is dangerous and may distort the dynamometer results. A variation of this attempt has been to shorten dynamometer testing by alternating use of hot and cold water in the cooling jacket and use of hot and cold air in the distributor of the assembled engine. This procedure also may not produce accurate fatigue data. Yet still another attempt to shorten dynamometer testing has been to increase the test temperature by use of an overload condition but limited to an initially short period of time, such as three minutes at a temperature level of about 334° C.; this is followed by normal engine loadings to provide a test temperature of about 254° C. for another three minute interval. Such initially high loading followed by moderate loading requires at least 1500 cycles for a small engine to induce cracking. This approach is undesirable because of the need to run a significant number of engines at high cost.

Applicant is unaware of any devices to totally eliminate the need for dynamometer testing of automotive engine components. However, some devices have been created to simulate and accelerate thermal stress conditions for non-automotive elements, such as those used in the aerospace industry. These devices are characterized by high equipment and operating costs, or by the need for an extremely high number of cycles to induce fatigue cracking. One of these devices has used alternate test chambers containing gaseous nitrogen and cryogenic fluids; another used hot liquids to impact test specimens to exert mechanical as well as thermal stresses, alternately utilizing heated and cooled air. All these alternative various devices suffer from either high cost or the test is insufficiently accelerated to be desirable for automotive industry use.

SUMMARY OF THE INVENTION

It is an object of this invention to provide a cheaper method and apparatus that more effectively and more rapidly determines the thermal fatigue life of a combustion chamber test specimen.

The inventive method that fully meets the above object, comprises; (i) impinging one or more torch flames directly on a selected area of the test specimen (i.e. metallic engine cylinder head) to heat such area to a critical test temperature that exceeds the normal maximum loading temperature of the specimen in normal use by about 10–25%, and holding such temperature for a period of 0.01–2.0 minutes; (ii) at the end of the holding period, quench the heated area of the test specimen to a temperature that is about 75% below that of the normal maximum loading temperature and holding such quenching temperature for about 1–3 minutes; and (iii) repeating steps (i) and (ii) until a crack is induced in the test specimen while recording the history of temperature and time involved in such repeated steps.

It is preferable to quench by direct pressurized water streams for optimal acceleration of the test, but cooling fluids, functioning in the water jacket channels of the head may be substituted for direct stream quenching; alternatively hot and cold air may be forced through the intake and exhaust ports of the cylinder head to achieve some degree of quenching.

The inventive apparatus aspect of this invention comprises a system having: (a) a heating enclosure supporting a metallic cylinder head; (b) a plurality of torches extending into such enclosure for impinging flames on selected areas of the head, the torches carrying a combustible mixture of air and fuel in a ratio of about 10 to 1, that can provide a flame that heats the areas from room temperature to a temperature of at least 250° C. in a period of less than 1 minute; (c) a plurality of quenching nozzles with at least one nozzle associated with each area for directing quenching fluid thereonto for a selected time interval; (d) controlled means for cycling the operation of the torches and nozzles, wherein a cycle can be repeated which cycle consists of quickly heating the selected areas of the head to said temperature and holding for a period of 0.01–2.0 minutes at the end of which time a nozzle administers quenching fluid that rapidly reduces the head temperature by at least 200° C. for a period of 1–3 minutes.

DETAILED DESCRIPTION AND BEST MODE

Figure 1:
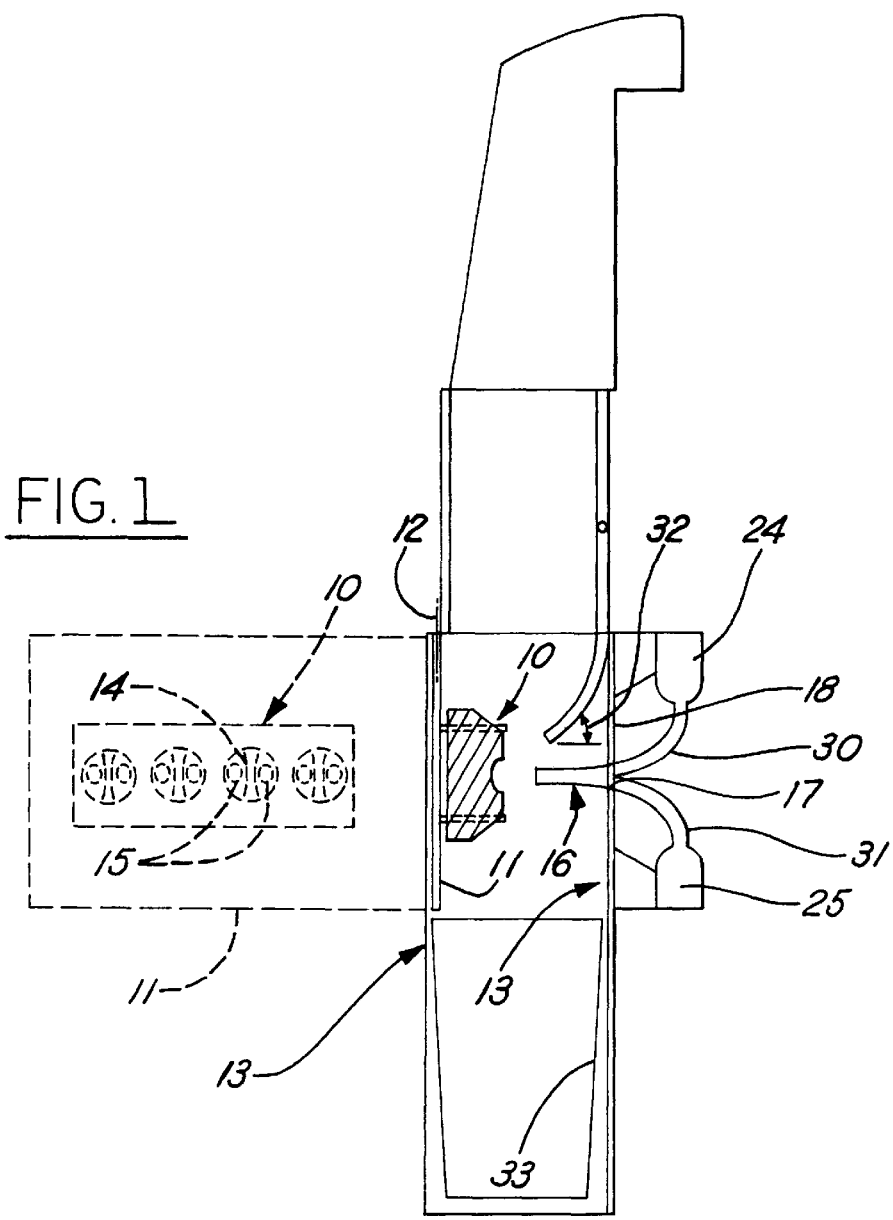
FIG. 1 is a sectional elevational view of the heating enclosure and apparatus for carrying out the accelerated thermal fatigue test regime in accordance with this invention.
Figure 3:
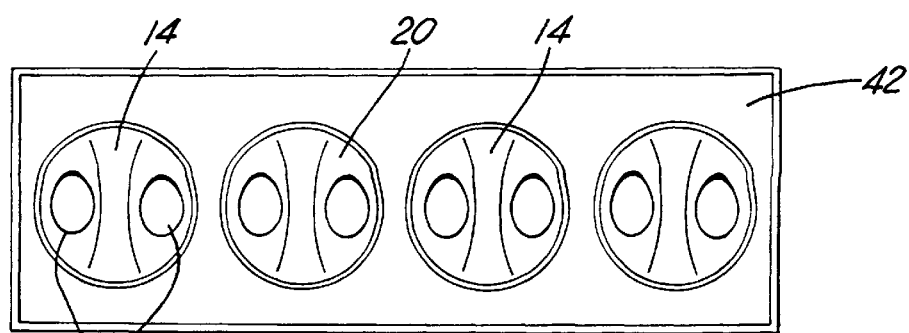
FIG. 3 is an enlarged sectional view of one side of the cylinder head under test (showing the related areas to be heated) taken along lines 3—3 of FIG. 1.
Figure 2:
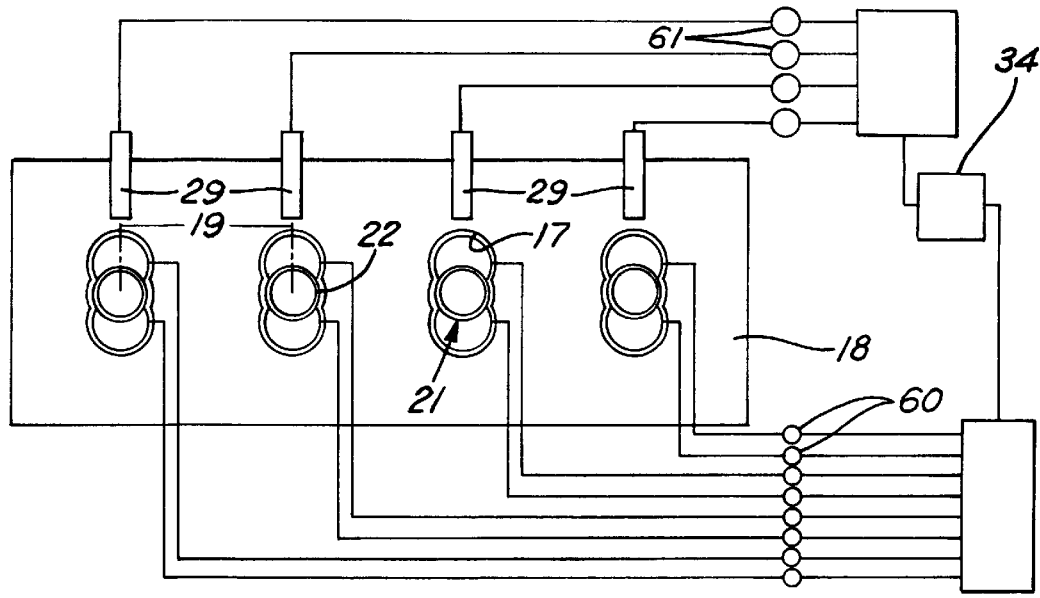
FIG. 2 is a sectional view of a portion of FIG. 1 taken along line 2—2 thereof.
Figure 4:
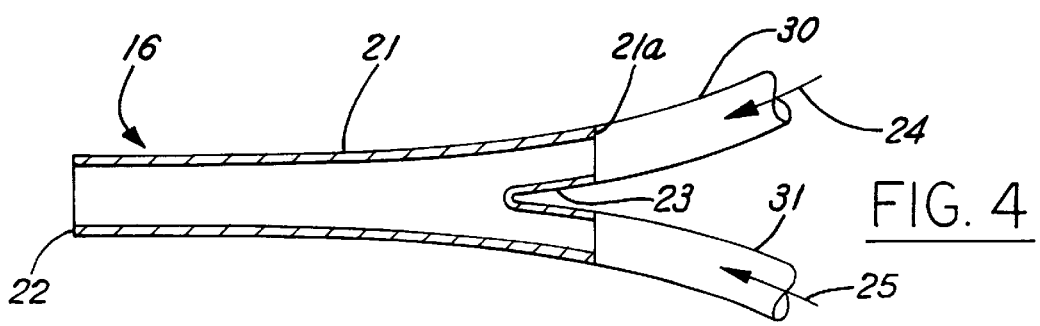
FIG. 4 is a greatly enlarged sectional view of a portion of a torch, taken along line 4—4 of FIG. 1.

As shown in FIG. 1, a test specimen 10 (engine cylinder head) is mounted on plate or fixture 11 which is swingable about an axis 12 secured to cabinet or test chamber 13 forming a heating envelope or chamber; the plate 11 is swingable in and out of the cabinet 13 for ease of mounting and exposing the head for inspection. Areas of the head 10 which will endure the greatest thermal stress in use are usually the metallic bridge areas 14 disposed between the valve ports 15 (see FIG. 3). A plurality of burners or torches 16 extend through access openings 17 in the side 18 of the cabinet 13 and are generally spaced at 19 to align with the targeted bridge areas 14 on a combustion wall 20 of a typical automotive engine head. As shown in FIG. 4, each torch 16 is comprised of a gas mixing tube 21 having a circular nozzle end 22 with a diameter of about 1.5–2.5 inches; the tube is formed of steel and has a wall thickness of about 0.5". The tube has a bifurcation 23 at its opposite end 21a to secure separate pressurized supplies of natural gas 24 and air 25 carried by respective lines 30, 31. The respective pressures of such supplies are 7 psi and 10 psi. The natural gas and air are mixed in a ratio of about 1:10. If the ratio deviates more than 5% from this set ratio, certain disadvantages will follow, such as reduced heating stress resulting in inadequate temperature differential between heating and quenching.

Figure 5:
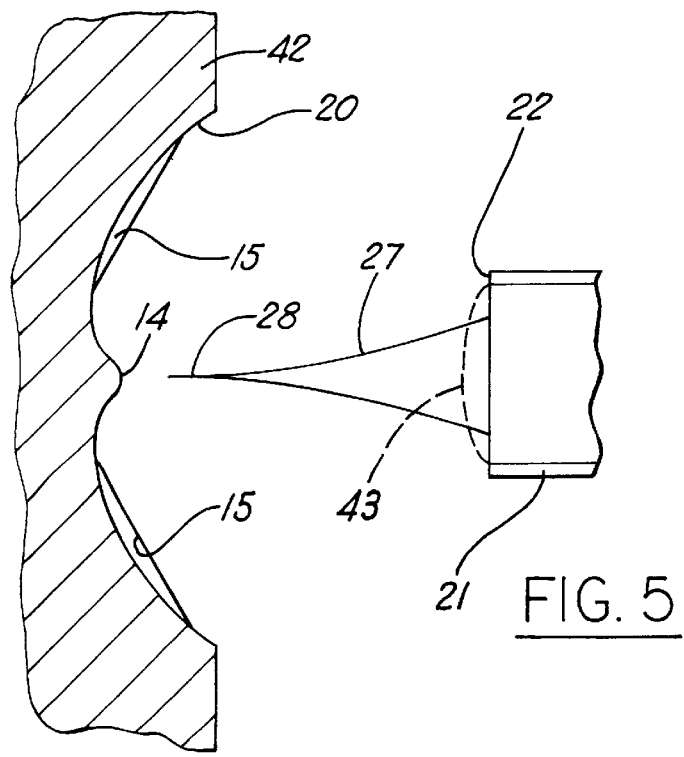
FIG. 5 is a greatly enlarged view of the circled portion of FIG. 1, illustrating the flame shape emanating from the torch.

As shown in FIG. 5, the size or shape of the flame 27 projecting from the nozzle 22 (when the fuel/air mixture is ignited at the nozzle) will taper to a sharp needle point 28 that should contact or be adjacent the bridge area 14 as desired; in this manner, the hottest blue flame tip can impart the desired degree of thermal stress.

Water quenching nozzles 29 extend through the cabinet wall 18 and depend at an angle 32 relative to the alignment between the torch and bridge area 14; the quenching nozzles 29 are also aimed at areas 14. Quench water, after contacting the areas 14, falls into a collection tank 33 for recirculation and temperature control. Quench water is supplied at a pressure of about 30–60 psi and at an ambient temperature of about 20° C.

Figure 8:
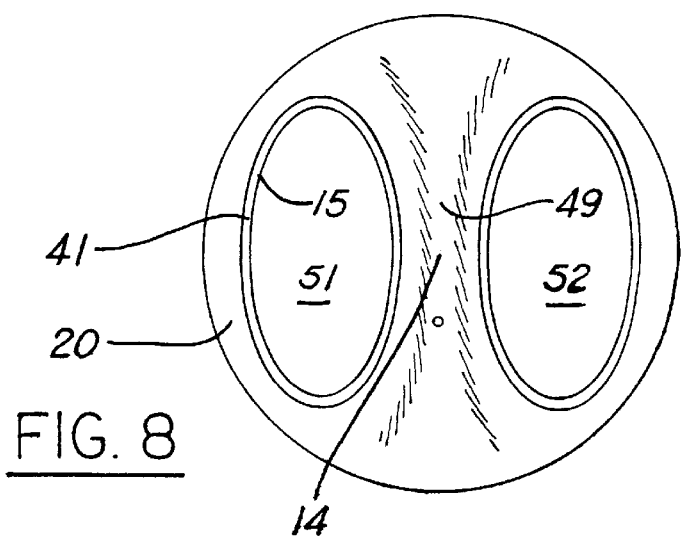
FIG. 8 is a greatly enlarged view of the circled portion of FIG. 3 illustrating how a thermal fatigue crack is eventually initiated and propagated.

The flow of gasses and water are controlled by a closed loop timed feedback control 34 which comprises timing valves 60 and 61 for admission and modulations of gas and air, as well as microsensors for flow and temperature (see temperature sensor 40 in FIG. 8). As many as 12–15 temperature sensors may be placed in the walls of the cylinder head.

Figure 6:
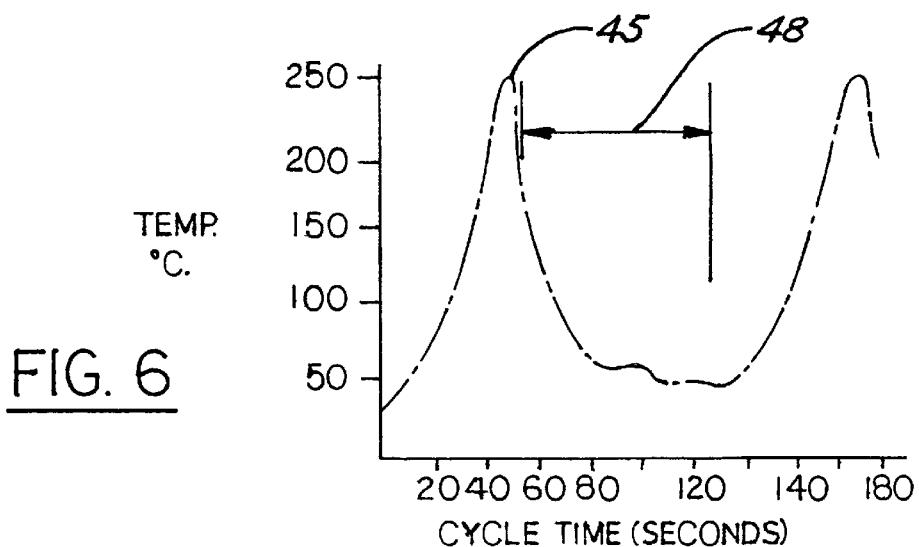
FIGS. 6 and 7 are graphical representations of test data generated using this invention, each representation using a different heating profile.
Figure 7:
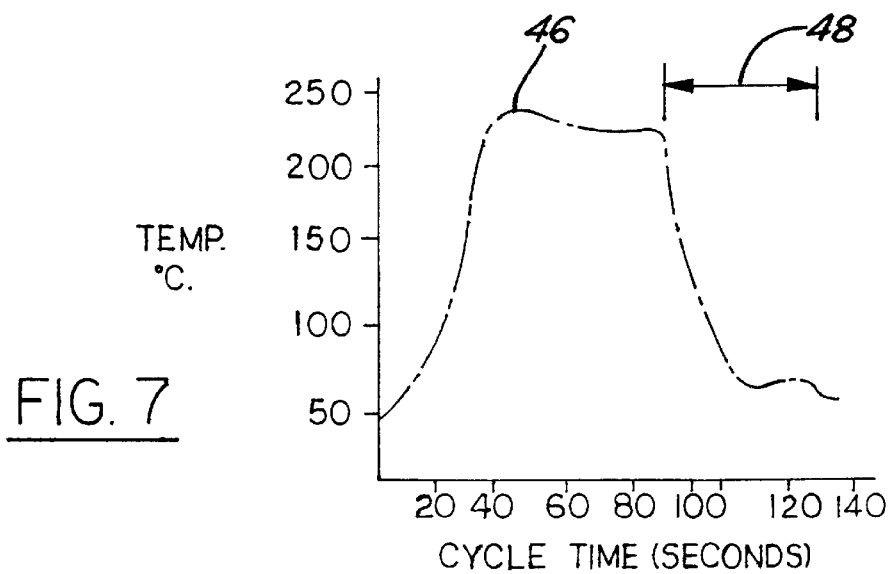

To carry out a test regime, the test specimen (cylinder head 10), has thermocouples 40 embedded at areas to be monitored, such as in the bridge area 14; the specimen is mounted on plate 11 with bolts torqued to the same force as used in a fully assembled engine. The head is swung into position with its combustion chambers walls 20 aligned with the axes of the torches and is spaced about 4–6 inches from the end of the torch nozzles. Although it is preferably to test a raw bulk cylinder head, the head may contain valve seat inserts 41 and gaskets 42, or even the valve train, normally employed in an engine that is assembled. Prior to starting the heating cycle, each torch will have a pilot flame 43; upon initiation of the cycle, the combustion gas pressure is increased and the flame converts to a full shape 27 which is several inches in length (as shown in FIG. 5) and is sufficient to reach and impinge upon the bridge area. Initiation of impingement becomes the start time for the test; the test specimen will heat up from ambient temperature to the test temperature (designed for the metal material and thickness under test) which is usually about 250° C. for an aluminum cylinder head having a wall thickness of about 8–10 mm. When either the target maximum temperature 45 is sensed in the target area (i.e. bridge area 14) as shown by the temperature profile in FIG. 6, or the target maximum temperature 46 is permitted to dwell for a period of about 1 to 2 minutes as shown in profile in FIG. 7 (to promote a homogenized temperature throughout the head combustion chamber), the torch flame is reduced to a pilot condition 43 and the target area is quenched by a stream of water splashed thereon, which water falls to the collection tank below and is recirculated for use. The quench interval 48 continues for about 1–3 minutes, and the heating cycle repeats itself after completion of the quench interval. The cycles are continuously repeated until a crack 49 occurs in the test specimen. This usually begins to occur first as a fissure as shown in FIG. 8.

The maximum test temperature is designed with the following considerations in mind: peak temperature measured in a running engine, the thermal history of the cylinder head and the material. The size of the flame or plume can be diffused to heat the entire combustion chamber wall 18 or other areas of interest, but this will result in lower temperature in the critical intervalve bridge section. Crack initiation will usually occur in 600–1200 cycles depending on the head geometry, material chemistry and test temperature. Such cycles can be realistically accumulated within a period of about 24 hours.

If it is desired to simulate engine cooling conditions and its effect on thermal fatigue, the test regime may be operated with cooling fluid (water) passed through the water jacket of the cylinder head in lieu of water jets that would normally impinge on the selected areas to be quenched. This regime will usually result in an increase in the number of cycles to reach fatigue life because indirect heating is used and uniform heat (low temperature differential) may be achieved in the intervalve bridge section, a condition which delays conditions which favor thermal fatigue but it is informative because of similarity to operating conditions of an engine.

Alternatively, and again in lieu of water jet impingement, hot and cold air can be circulated through the exhaust and intake ports 51, 52, respectively, to induce cracks on the bridge areas. This heating and cooling regime will substantially increase the number of cycles to reach fatigue life by 100 times because of the need to keep water temperature below the boiling point.

By carrying out the test on raw heads in the bulk condition before they are machined to final size, considerable expense can be saved if machining is eliminated. The lack of machining makes no difference in the test because cylinder heads are not isotropic. The temperature and time data, when accumulated for two or more different component configurations, will indicate how shape, material or metallurgical heat treatment can be optimized to increase or control fatigue life.

While particular embodiments of the invention have been illustrated and described, it will be obvious to those skilled in the art that various changes and modifications may be made without departing from the invention, and it is intended to cover in the appended claims all such modifications and equivalents as fall within the true spirit and scope of this invention.

We claim:

1. A method of providing accelerated thermal fatigue testing of an engine combustion chamber wall comprising:
   (a) impinging one or more torch flames each directly on a selected area of said wall to heat such area to a critical test temperature that exceeds the normal maximum loading temperature of the chamber wall for normal use by about 10–25%, and holding such temperature for a period of 0.01–2.0 minutes;

(b) at the end of the holding period, quenching the heated area of the wall to a temperature that is about 75% below that of the normal maximum loading temperature and holding such quenching temperature for a period of about 1–3 minutes; and (c) repeating steps (a) and (b) until a crack is induced in the wall of the combustion chamber, while recording the history of temperature and time involved in such repeated steps.

2. The method as in claim 1, in which the combustion chamber wall is constituted of aluminum or aluminum alloy and the critical test temperature is about 250° C.

3. The method as in claim 2, in which the temperature to which the combustion chamber wall is quenched is about 45° C.

4. The method as in claim 1, in which said quenching is carried out by the use of direct impingement of pressurized water streams that impinge and flood the selected areas.

5. The method as in claim 1, in which water jacket channels are associated with said engine chamber and said quenching is carried out by use of cooling fluids functioning in said water jacket channels to operate as the only means of quenching.

6. The method as in claim 1, in which said intake and exhaust ports are associated with said engine chamber wall, and said quenching being carried out by use of hot and cold air that are respectfully forced through the intake and exhaust ports to achieve some degree of quenching.

7. The method as in claim 1, in which the ratio of combustible gas and air for purposes of creating the torch flame is about 1:10.

8. An apparatus for carrying out accelerated thermal fatigue testing of an engine combustion chamber, comprising;

(a) a heating enclosure supporting a metallic automotive cylinder head therein;

(b) a plurality of torches extending into such enclosure for impinging flames on selected areas of the head, each torch carrying a combustible mixture of air and fuel in a ratio of about 10 to 1 and providing a flame that heats the areas from room temperature to a temperature of at least 250° C. in a period of less than one minute;

(c) a plurality of quenching nozzles extending into such enclosure, with at least one nozzle associated with each selected area for directly quenching fluid thereonto for selected time periods; and (d) control means for cycling the operation of the torches and water nozzles wherein a cycle is repeated that consists of quickly heating the selected area of the head and holding for a period of 0.01–2 minutes, at which time quenching fluid rapidly reduces the head temperature by at least 200° C. for a period of 1–3 minutes.

* * * * *